United States Patent [19]

Chervitz

[11] Patent Number: 4,917,699
[45] Date of Patent: Apr. 17, 1990

[54] PROSTHETIC LIGAMENT

[75] Inventor: Alan Chervitz, Palm Harbor, Fla.

[73] Assignee: Zimmer, Inc., Warsaw, Ind.

[21] Appl. No.: 194,323

[22] Filed: May 16, 1988

[51] Int. Cl.$^4$ ............................................. A61F 2/08
[52] U.S. Cl. ..................................... 623/13; 87/8
[58] Field of Search ............... 623/13; 87/7, 8, 5, 87/6

[56] References Cited

U.S. PATENT DOCUMENTS

| | | | |
|---|---|---|---|
| 4,149,277 | 4/1979 | Bokros | 3/1 |
| 4,301,551 | 11/1981 | Dore et al. | 3/1 |
| 4,483,023 | 11/1984 | Hoffman, Jr. et al. | 3/1 |
| 4,506,681 | 3/1985 | Mundell | 128/92 |
| 4,535,768 | 8/1985 | Hourahane | 128/305.1 |
| 4,584,722 | 4/1986 | Levy et al. | 623/13 |
| 4,590,928 | 5/1986 | Hunt et al. | 128/92 |
| 4,605,414 | 8/1986 | Czajka | 623/13 |
| 4,610,688 | 9/1986 | Silvestrini et al. | 623/1 |
| 4,621,560 | 11/1986 | Brown et al. | 87/8 |
| 4,662,886 | 5/1987 | Moorse et al. | 623/13 |
| 4,668,233 | 5/1987 | Seedhom et al. | 623/13 |
| 4,719,837 | 1/1988 | McConnell et al. | 87/5 X |
| 4,728,329 | 3/1988 | Mansat | 623/13 |
| 4,731,084 | 3/1988 | Dunn et al. | 623/13 |

FOREIGN PATENT DOCUMENTS 0192949 3/1986 European Pat. Off. .
2151487 2/1985 United Kingdom .

OTHER PUBLICATIONS

Integraft Stent System; DePuy, date unknown.
CFS Ligaments, Plastafil, date unknown.
Advanced Textile Braiding Techniques, Brown et al., Atlantic Research Corporation, date unknown.
Technical Report AFML TR-70-28.3, Stover et al., Mar. 1971.

Primary Examiner—Alan W. Cannon
Attorney, Agent, or Firm—Paul David Schoenle

[57] ABSTRACT

A prosthetic ligament is constructed from a three-dimensional braider. The prosthetic ligament includes an eyelet at a first end and a pigtail at a second end. The pigtail is removed during surgery so that the remaining implantable prosthetic ligament is defined by a continuous three-dimensional braided structure from the eyelet at the femur to the other end at the tibia.

2 Claims, 2 Drawing Sheets

PROSTHETIC LIGAMENT

The present invention covers a prosthetic ligament which is implanted to repair or replace existing ligament tissue in a body.

Heretofore, prosthetic ligaments have been proposed which are formed from a collection of loosely bundled fibers. These fibers are sometimes wrapped in an open sheath to encourage tissue growth into the sheath and fibers for fixation of the prosthetic ligament to bone. Other prosthetic ligaments provide a coreless tubular structure to accommodate bone plugs or the like in the tubular ends. These prior art prosthetic ligaments address the problem of fixation as the prosthetic ligament is subjected to substantial loads and loosening of the prosthetic ligament is to be avoided.

In addition, the material of the prosthetic ligament must be compatible with other body tissue and at the same time resist abrasion in response to movement of bone against the surface of the prosthetic ligament. It has been proposed that different fibers can be joined together to accommodate elasticity and yield strength in a triaxially braided construction.

The present invention provides a prosthetic ligament constructed from one biocompatible material which is utilized in a three-dimension braid to accommodate the characteristics of strength and elasticity. It is believed that the three-dimension braiding provides the optimal orientation for a plurality of fibers to substantially replicate the behavior of natural ligament. Moreover, the three-dimension braid for the prosthetic ligament provides for an eyelet of foldable, compressible material to enhance fixation to bone while a two-dimension braided pigtail extends from the three-dimension braid to assist the surgeon in directing the prosthetic ligament through bone channels.

It is an advantage of the present invention that a contiguously braided prosthetic ligament includes an eyelet at one end for ease in fixation to a bone while the other end of the contiguously braided prosthetic ligament defines a reduced diameter pigtail or the like for easy insertion through a bone tunnel. Moreover, the particular braid imparted to the prosthetic ligament is three-dimensional so that an individual strand of fiber extends in all directions within the prosthetic ligament to generate inherent strength and elasticity akin to that for natural ligaments. Additionally, fiber redundence is increased by three dimensional braiding, thus acting as crack stoppers.

In the drawings

Figure 1:
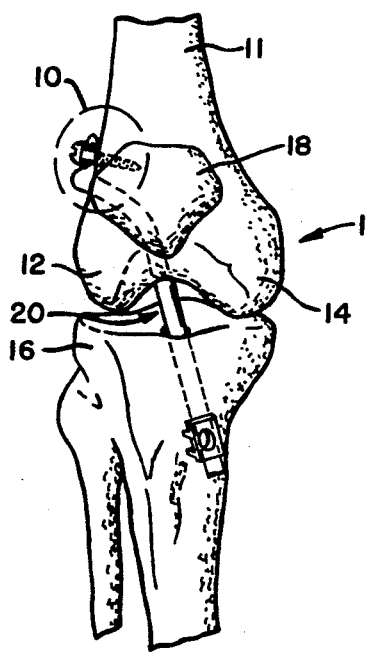
FIG. 1 is a schematic illustration of an anterior cruciate ligament prosthesis extending between a femur and a tibia in a human knee joint.

The human knee joint 10 includes a femur 11 with condyles 12 and 14 adapted for articulation with respect to a tibial plateau 16. A patella 18 helps to orientate a patella tendon (not shown). Extending from the distal lateral side of the femur to the proximal medial side of the tibia is a prosthetic ligament 20 constructed in accordance with the present invention and intended to take the place of the natural anterior cruciate ligament which was surgically removed. The prosthetic ligament 20 cooperates with the femur and the tibia to oppose separation between these bones while also permitting articulation and slight extension during normal movement between the femur and tibia.

Figure 2:
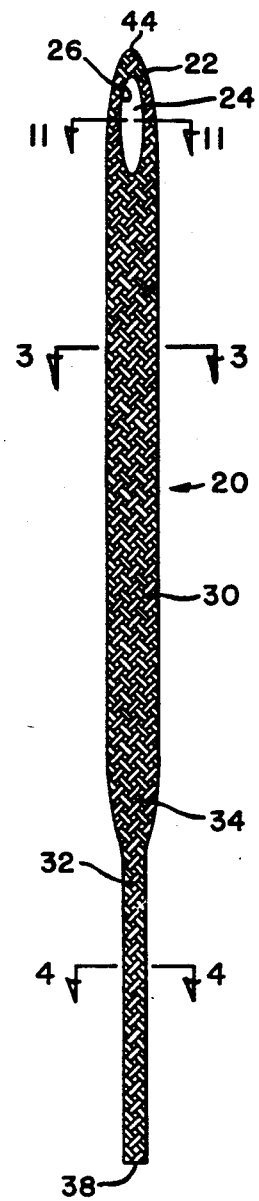
FIG. 2 is a side view of a prosthetic ligament as it exists prior to implantation.
Figure 3:
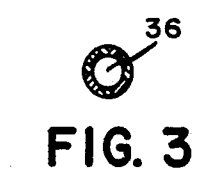
FIG. 3 is a cross-sectional view taken along line 3—3 of FIG. 2.
Figure 4:
FIG. 4 is a cross-sectional view taken along line 4—4 of FIG. 2.

In FIG. 2 the prosthetic ligament 20 defines a first end 22 with an eyelet 24 formed by a pair of interconnected apertures 26 and 28 on opposite sides of the first end 22. An intermediate section 30 extends from the first end 22 to a second end 32. A transition zone 34 between the intermediate section 30 and the second end 32 provides for a reduction in the diameter of the prosthetic ligament between the intermediate section 30 and the second end 32. As shown in FIGS. 3 and 4, the prosthetic ligament 30 is constructed in tubular form, as more fully described hereinafter, with an inner diameter defining a canal 36 extending from an opening 38 at the second end 32 to the eyelet 24. The radial dimension for the intermediate section 30 is substantially uniform from the first end to the transition zone 34 and the radial dimension for the second end 32 is substantially uniform from the transition zone 34 to the opening 38.

The prosthetic ligament 32 is constructed in a braiding operation using Ultra High Molecular Weight Polyethylene (UHMWPE) fibers extruded to 38 microns. This material is available from Allied-Signal Company pursuant to their designation Spectra 900-1200 Denier. The braiding operation is a three-dimensional braid as distinguished from a two-dimensional braid. Heretofore, three-dimensional braiding has been utilized in the aerospace, electronic and defense industry for the construction of missile, computer and ship components, respectively. Apart from this application, no orthopaedic or medical application is known or suggested for a three-dimensional braid. A discussion of three-dimensional braiding is found in "Advanced Textile Braiding Techniques" Richard T. Brown and Mabel E. Harman, Atlantic Research Corporation, Presentation at the Conference on Advance in High Performance Component Technology, Clemson University, Clemson, S.C. (date unknown). See also U.S. Pat. No. 4,312,261 issued Jan. 26, 1982 to Robert A. Florentine and "Preparation of an Omniweave-Reinforced Carbon/Carbon Cylinder As A Candidate For Evaluation In The Advanced Heat Shield Screening Program" Technical Report AFML-TR-70-283 March 1971. Air Force Materials Laboratory, Air Force Systems Command, Wright-Patterson Air Force Base, Ohio.

Figure 5:
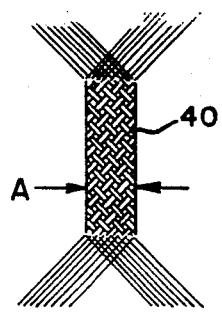
FIG. 5 is a schematic front view of a braided panel utilized to commence manufacture of the prosthetic ligament illustrated in FIG. 2.
Figure 6:
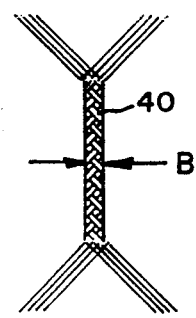
FIG. 6 is a side view of FIG. 5.
Figure 7:
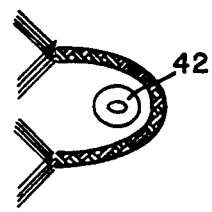
FIG. 7 is a schematic side view of the second step in the manufacturing process for constructing the prosthetic ligament.
Figure 8:
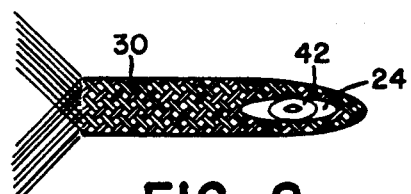
FIG. 8 is a schematic side view of the third step in the manufacturing process for constructing the prosthetic ligament.
Figure 9:
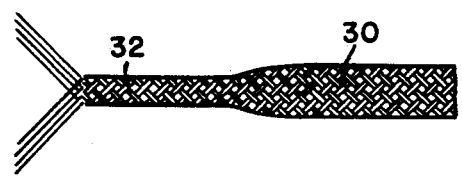
FIG. 9 is a schematic side view of the fourth step in the manufacturing process for constructing the prosthetic ligament.

In FIG. 5, a braided section of rectangular structure 40 is formed in a three-dimensional braider with 118 fibers per yarn and 2 yarns per carrier. For the prosthetic ligament of the present invention it is preferred to use 54 carriers and 108 yarns. The width A of the flat panel 40 is about four times wider than the thickness B. After a predetermined length of the braided flat panel 40 is formed in the three-dimensional braider, the length is disposed over a fixture or mandrel 42 in FIG. 7 to initiate the formation of the eyelet 24. The length of flat panel 40 dictates the size of the eyelet opening. Continued three-dimensional braiding forms a tubular construction for the intermediate section 30 until the desired length of the intermediate section is obtained. At this time, some yarns are terminated with each machine cycle at or near the inner wall of the tubular construction forming the tapering transition zone 34. Continued braiding forms the end section 32. If a sufficient number of yarns are terminated in transition zone 34, the resulting end section 32 will be two-dimensionally braided rather than three-dimensionally braided. The ends of the terminated yarns are entrapped within the transition zone 34, and the fewer yarns in the end section 32 results in the smaller diameter of the end section 32. When the desired length for the end section 32 is reached, all of the yarns are cut from the end section 32 to form the opening 38.

Figure 10:
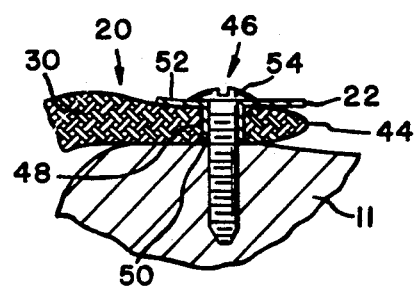
FIG. 10 is a side view, partly in cross-section, of the attachment device for the prosthetic ligament at the femur.
Figure 11:
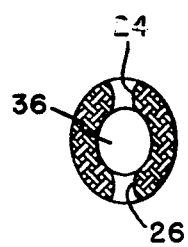
FIG. 11 is a cross-sectional view taken along line 11—11 of FIG. 2.

As noted in FIGS. 5–8, the flat panel 40 is initially transformed about the fixture 42 into a C-shaped trough and secondly into a tubular structure for the intermediate section 30. During this transformation, the sides or walls of the prosthetic ligament at 90° to the openings 24 and 26 bulge outwardly, see FIG. 11. In addition, a tip 44 at the first end 22 is substantially arcuate. With this geometry for the first end 22 adjacent the eyelet 24, a fixation device 46 shown in FIG. 10 is adapted to fit within the eyelet 24. The device 46 comprises a bushing 48 with a cylindrical boss 50 and an almost flat top 52. A bone screw 54 extends through the cylindrical boss 50 with a head of the screw abutting the flat top 52. The prosthetic ligament first end 22 is compressed between the femur 11 and the flat top 52 such that a top side adjacent opening 26 overlaps or approaches a bottom side adjacent opening 28 resulting in a folding of the first end 22 at the point of fixation to the femur 11.

In view of the foregoing description, it is seen that the prosthetic ligament 20 comprises a braided structure from the second end 32 to the first end 22. The reduced diameter for the second end 32 presents a pigtail or lead for a surgeon to easily direct that end through a bone tunnel prepared in the femur and tibia. The first end 22 is substantially toroidal about the eyelet 24 to provide for a folded attachment to the femur. This folded attachment is believed to further accommodate the transfer of loads from the prosthetic ligament to the femur. With the attachment device 46 securely fastening the prosthetic ligament to the femur, it is possible for the surgeon to impart the desired tension to the ligament by pulling on the pig tailed second end. At this time, a staple or suitable clamp may be positioned over the intermediate section 30 as it extends outwardly of the tibia tunnel and driven into the tibia. The remaining intermediate section 30, transition zone 34, and second end 32 are then cut off. The second end is not intended for utilization as an implantable prosthetic ligament but instead is provided for assistance in disposition of the prosthetic ligament within the bone tunnels in the femur and tibia.

Although the foregoing description proceeds with reference to the eyelet 24 being attached to the femur, it is well known that such eyelet can also be attached to the tibia with the second end extending outwardly from the femur bone tunnel.

I claim:

1. A prosthetic device for repair or replacement of tissue connected to a bone, the prosthetic device including a first end with an eyelet to receive fixation means for securing the first end to the bone, a second end of reduced outer diameter for insertion into a tunnel formed in the bone, and an intermediate section connecting the first end and the second end, the second end and intermediate section defines a canal extending from an opening at the second end to an opening at the eyelet at the first end, the first end and the intermediate section being formed with a first uniform braid of a plurality of fibers and the second end being formed with a second uniform braid from a portion of the plurality of fibers, the second uniform braid being different from the first uniform braid wherein said first uniform braid is defined by a three dimensional braid for the plurality of fibers, the second end serving as a guide for insertion of the second end through the bone channel so that the intermediate section adjacent the second end is adapted for fixation to another bone and the second end is cut off after the first end and intermediate section are secured to bone.

2. The prosthetic device of the claim 1 in which the second uniform braid is defined by a two-dimensional braid for the portion of the plurality of fibers.

* * * * *